United States Patent
Begon et al.

(10) Patent No.: US 9,204,989 B2
(45) Date of Patent: Dec. 8, 2015

(54) DYNAMIC SHOULDER ORTHOSIS WITH REHABILITATING ADDUCTION

(71) Applicants: Mickael Begon, Montreal (CA); Jacinte Bleau, Rawdon (CA); Serge Nobert, Montreal (CA); Patrice Tétreault, Ville Mont-Royal (CA)

(72) Inventors: Mickael Begon, Montreal (CA); Jacinte Bleau, Rawdon (CA); Serge Nobert, Montreal (CA); Patrice Tétreault, Ville Mont-Royal (CA)

(73) Assignees: Universite de Montreal, Montreal, Quebec (CA); 2330-2029 Quebec, Inc., Montreal, Quebec (CA)

(*) Notice: Subject to any disclaimer, the term of this patent is extended or adjusted under 35 U.S.C. 154(b) by 197 days.

(21) Appl. No.: 14/019,757

(22) Filed: Sep. 6, 2013

(65) Prior Publication Data

US 2015/0073323 A1    Mar. 12, 2015

(51) Int. Cl.
*A61F 5/00* (2006.01)
*A61F 5/37* (2006.01)

(52) U.S. Cl.
CPC .................................. *A61F 5/3753* (2013.01)

(58) Field of Classification Search
CPC ....... A61F 5/026; A61F 5/3753; A61F 5/028; A61F 5/3738; A61F 5/0102; A61F 5/013; A61F 5/3746; A61F 2005/0134; A61F 2005/016; A61F 2005/0167; A61F 5/0125; A61F 5/024; A61F 5/055; A61F 5/00; A61F 5/05858; A61F 5/02; A61B 5/0531; A61B 5/11; A61B 5/165; A61B 5/6812
USPC ................................ 128/845; 602/4–5, 19–22
See application file for complete search history.

(56) References Cited

U.S. PATENT DOCUMENTS

| | | | |
|---|---|---|---|
| 1,257,297 A | | 2/1918 | Brown |
| 1,639,815 A | | 8/1927 | Siebrandt |
| 2,191,283 A | | 2/1940 | Longfellow |
| 2,310,566 A | * | 2/1943 | Anderson ................. 602/19 |
| 2,661,000 A | | 12/1953 | Gazeley et al. |
| D244,152 S | | 4/1977 | Kvittingen |
| D266,948 S | | 11/1982 | Kvittingen |
| 4,598,701 A | | 7/1986 | Schaefer |
| 4,751,923 A | * | 6/1988 | Marino ...................... 602/4 |
| 4,878,490 A | | 11/1989 | Scott |

(Continued)

FOREIGN PATENT DOCUMENTS

| | | |
|---|---|---|
| EP | 0192181 A2 | 8/1986 |
| EP | 0737455 A2 | 10/1996 |

(Continued)

*Primary Examiner* — Michael Brown
(74) *Attorney, Agent, or Firm* — Fraser Clemens Martin & Miller LLC; James D. Miller

(57) ABSTRACT

A shoulder orthosis for long term support of a patient's arm in postoperative shoulder immobilization posture for rotator cuff tears, comprising a waist belt, an arm splint, and a piston and cylinder assembly interconnecting the waist belt to the splint and biasing the splint to an abduction upper limit position. The orthosis provides stable support of the forearm about a horizontal plane, while enabling both pivotal movement of the arm about a vertical axis intersecting the patient's elbow and towards or away from the patient's torso within this horizontal plane. This orthosis also enables cyclical up and down motion of the splint, the downward motion being healthy adductor-assisted against the bias of the piston and cylinder assembly. A lock system releasably locks the piston and cylinder at a selected retracted position of the piston rod.

20 Claims, 14 Drawing Sheets

(56) References Cited

U.S. PATENT DOCUMENTS

| | | |
|---|---|---|
| 4,896,660 A | 1/1990 | Scott |
| 4,930,523 A | 6/1990 | Laico et al. |
| 5,033,461 A * | 7/1991 | Young et al. .................... 602/16 |
| 5,046,490 A | 9/1991 | Young et al. |
| 5,383,844 A | 1/1995 | Munoz et al. |
| 5,385,536 A * | 1/1995 | Burkhead et al. ............... 602/20 |
| 5,423,333 A | 6/1995 | Jensen et al. |
| 5,487,724 A | 1/1996 | Schwenn |
| 5,520,620 A | 5/1996 | Johnson |
| 5,718,671 A | 2/1998 | Bzoch |
| 5,961,512 A | 10/1999 | Purnell |
| 6,110,133 A | 8/2000 | Ritts |
| 7,255,679 B2 | 8/2007 | Kania et al. |
| 7,320,669 B2 | 1/2008 | Campbell et al. |
| 7,819,827 B2 | 10/2010 | Pellinen |
| 2005/0159693 A1 | 7/2005 | Sims |
| 2007/0191751 A1 | 8/2007 | Ruff |
| 2010/0121236 A1 | 5/2010 | Goumas |

FOREIGN PATENT DOCUMENTS

| | | |
|---|---|---|
| EP | 1645251 A2 | 4/2006 |
| EP | 1645251 A3 | 7/2006 |
| WO | 9406518 A1 | 3/1994 |
| WO | 9500210 A1 | 1/1995 |
| WO | 03035185 A1 | 5/2003 |
| WO | 03071994 A2 | 9/2003 |
| WO | 2006097619 A1 | 9/2006 |
| WO | 2007030251 A2 | 3/2007 |
| WO | 2007067929 A2 | 6/2007 |
| WO | 2008065701 A1 | 6/2008 |
| WO | 2009092348 A1 | 7/2009 |

* cited by examiner

DYNAMIC SHOULDER ORTHOSIS WITH REHABILITATING ADDUCTION

FIELD OF THE INVENTION

The present invention relates to shoulder orthosis for supporting the arm in abduction after a surgical repair of tear injuries to the rotator cuff, and more specifically to shoulder orthosis with adjustable arm stabilisation height enabling cyclical exercising of the uninjured arm adductor muscles.

BACKGROUND OF THE INVENTION

Muscle tears are degenerative type bodily injuries, whose occurrence increase with old age, in particular beyond 70 to 80 years of age. Shoulder muscle tear injuries occur typically when a person repetitively lifts heavy loads above his/her head, and will appear regularly in activities such as swimming, window cleaning, freight handling, strength conditioning exercising, and the like.

It often happens that an important part of the medical treatment of a repaired shoulder muscle requires the stabilization and support of the arm in abduction (away from the patient's sagittal plane) during the rehabilitation healing period which typically lasts between four to twelve weeks, and in general about six weeks. Shoulder muscular injuries can be of different types involving different set of muscles. Different medical treatments involving surgery may be required depending on the injury type and severity. In each case, proper healing requires that the patient's arm be stabilized at a specific angle relative to the body to maintain the shoulder in the ideal position. As the healing progresses, the arm stabilization angle is often reduced, bringing the arm in adduction (closer to the patient's sagittal plane) i.e. gradually closer to its natural position along the body. Furthermore, these injuries typically affect only part of the muscles of the shoulder, often being the supraspinatus (with possibly the infraspinatus) muscle with muscle tear length varying usually between 1 and 20 mm.

After an initial healing period, treatments exercising of the uninjured healthy muscles of the shoulder including the pectoralis major muscle, and possibly the latissimus dorsi muscle—are recommended to maintain tonus of these healthy muscles. This exercising is limited to a certain set of movements that minimize the use of the injured or repaired muscles. For example, in many types of injuries to the rotator cuff, it is recommended after a certain healing period for the patient to repeatedly exercise his/her adduction muscles.

Many of the shoulder orthosis and arm stabilization apparatuses known in the art are used to stabilize the arm in a single static given position. Others offer adjustment mechanisms enabling to change the height at which the arm is stabilized. But these height adjustment mechanisms often require external intervention and cannot be operated unaided by the patient alone. Some also require complex or lengthy procedures, requiring the orthosis to be firstly removed, or involving spare parts and even special tools. Some also comprise unstable harnesses and splint, or they comprise multiple support structures which are often cumbersome and uncomfortable. Furthermore, most of these orthosis do not enable any kind of free arm movement by the patient's arm, which is a major inconvenience when several weeks of rehabilitation are required.

Furthermore orthosis known in the art do not allow for the concurrent flexion/extension of the forearm around the injured arm elbow.

SUMMARY OF THE INVENTION

The present invention relates to a shoulder orthosis for surgically repaired rotator cuffs, and more specifically to surgically repaired rotator cuff muscles following tear of the supraspinatus muscle group only or to the supraspinatus and infraspinatus muscles. The present shoulder orthosis enables the exercising of the patient's arm healthy adduction muscles of the arm while minimizing contraction and stress of the injured muscles in the rotator cuff. The present shoulder orthosis also enables the flexion/extension of the forearm around the elbow while keeping the arm generally horizontal at a constant height. The present shoulder also stabilizes the arm at different angle relative to the body nature, severity and level of healing of the injury.

The flexion/extension of the elbow without displacement of the arm, since the elbow is coaxial to the piston, allows the activation of the elbow flexors/extensors (biceps and triceps), and also to be more functional and enabling the forearm to come closer to the patient's body. This will facilitate daily activities, such as coming across a narrow door frame, donning and wearing a coat, and drawing bedsheets over the patient's body when sleeping. The orthosis enables movement of the shoulder and of the elbow, to prevent "frozen shoulder" syndrome and stiffness in the joints.

Generally speaking, the present invention relates to a shoulder orthosis for long term support of a patient's arm in postoperative shoulder immobilization posture for rotator cuff tears, comprising a waist belt, an arcuate forearm support, and a piston and cylinder assembly interconnecting the waist belt to the forearm support and biasing the forearm support to an upper limit position. The orthosis provides stable support of the forearm about a horizontal plane, while enabling both pivotal movement of the arm about a vertical axis intersecting the patient's elbow and towards or away from the patient's torso within this horizontal plane. This orthosis also enables cyclical up and down motion of the forearm support, the downward motion healthy adductor-assisted against the bias of the piston and cylinder assembly. A lock system releasably locks the piston and cylinder at a selected retracted condition of the piston rod.

In particular, the present invention is directed at a shoulder orthosis for long term support of a patient's arm in postoperative shoulder immobilization abduction posture for injured rotator cuff muscle tear, said orthosis comprising: a waist belt member, releasably adjustably attachable to the patient's waist line; an arm splint, defining opposite outer and inner end portions and releasably adjustably attachable to the patient's arm; an extendible connector member, spacedly interconnecting a support section of said belt member to said splint inner end portion and defining a lengthwise axis thereof, wherein said splint is movable between a fully extended abduction first limit condition and a retracted adduction second limit condition, angularly relative to the patient's torso; damper means, cooperating with said connector member in biasing said splint away from said belt member, wherein said damper means enables cyclical back and forth extension/retraction of said extendible connector member between said first and second limit conditions thereof; locking means, releasably locking said extendible connector member at a selected condition against the biasing force of said damper means; and splint swing motion compensating means, providing transverse play of said connector member transversely of said lengthwise axis thereof, to accommodate inward rotation of the patient's arm naturally induced as the patient's arm is raised away from the patient's torso; wherein said orthosis enables cyclical exercising of the patient's arm healthy adduction muscles while minimising contraction of the injured muscles in the rotator cuff.

In one embodiment, said swing motion compensating means consists of a rotating member, integral to said connector member and enabling rotation of said splint relative to said connector member lengthwise axis, wherein said splint outer end portion is movable radially away from or towards the patient's torso.

In one embodiment, said damper means consists of an assembly made of a piston rod axially engaging a cylinder, said assembly integral to said extendible connector member, and of means continuously biasing said piston rod in extended condition away from said cylinder, said cylinder defining an outer end portion opposite said piston, and said piston rod defining a head opposition said cylinder. Said damper means could consist of a gas spring unit.

In one embodiment, said locking means consists of an elastic locking unit, cooperating with said gas spring unit, and a control member, controlling actuation of said locking means.

In one embodiment, said splint consists of: a channel member defining an arcuate panel, sized and shaped to conformingly receive and support a lower half portion of a patient's forearm, said arcuate panel having an inner end portion and an outer end portion, and a bed extending therebetween; forearm securing band members, integrally mounted to said arcuate panel intermediate said inner and outer end portions thereof and releasably engageable around an upper half portion of the patient's forearm; and a support anchor, integrally mounted transversely of said arcuate panel inner end portion and endwisely of said cylinder outer end portion. Said rotating member could consist of said piston rod being freely rotatably mounted axially within said cylinder. During the patient's arm flexion and extension back and forth radially relative to the patient's torso within the same horizontal plane, the pivotal axis of the patient's elbow remains coaxial at all times with the lengthwise axis of said piston rod and cylinder assembly.

In one embodiment, said belt member support section consists of an inner portion, shaped and sized to conformingly fit around the patient's trochanter portion, an integral outer pocket portion defining a pocket having a mouth, said piston rod head engaging through said pocket mouth and into said pocket, and a pivot mount member pivotally mounting said piston rod head to said pocket portion into said pocket and providing pivotal motion of said piston rod head about an axis transverse to said piston and cylinder assembly lengthwise axis. Said locking means control member could be mounted remotely from said piston and cylinder assembly, for example onto said belt member at a distance from said belt member support section.

In one embodiment, said forearm securing band members include adjustable hook and loop fastener means. Said waist belt member could also include adjustable hook and loop fastener means.

In one embodiment, there is further provided a palm rest tab, integrally projecting from said arcuate panel outer end portion, for supporting the patient's hand palm, said tab preferably having aeration bores, and being slightly transversely inclined and making a large acute angle relative to said arcuate panel bed, wherein the patient's arm wrist is maintained in slight extension.

Cushioning members could be carried inwardly of said belt member and ergonomically conforming to the patient's hip.

In one embodiment, during arm flexion and extension back and forth radially relative to the patient's torso, the pivotal axis of the patient's elbow remains coaxial at all times with the lengthwise axis of said piston rod and cylinder assembly.

In one embodiment, said arcuate panel inner end portion is of such a shape as to provide both a lateral support and an anteroposterior support for the patient's supported forearm.

The invention also relates to a method of use of a shoulder orthosis, said method comprising the following steps: attaching said waist belt to the patient's waist; securing the patient's arm to said arm splint; deactivating said locking means; and engaging the patient's adductor muscles to at least partly retract said connector member from said fully extended first limit condition towards said second limit condition thereof.

In one embodiment, the method also includes the steps of: releasing the patient's adductor muscle engagement; and allowing said damper means to extend said connector member to return to its said first fully extended limit condition.

In one embodiment, the method also includes the step of engaging once again the patient's adductor muscles to retract said connector member from said fully extended first limit condition towards its said second limit condition.

In one embodiment, the method also includes the step of rotating said arm support channel member relative to said waist belt member about said connector member, wherein flexion and extension of the patient's arm back and forth radially relative to the patient's torso is achieved, and wherein the pivotal axis of the patient's elbow remains coaxial at all times with the lengthwise axis of said connector member.

DETAILED DESCRIPTION OF THE EMBODIMENTS

Figure 1:
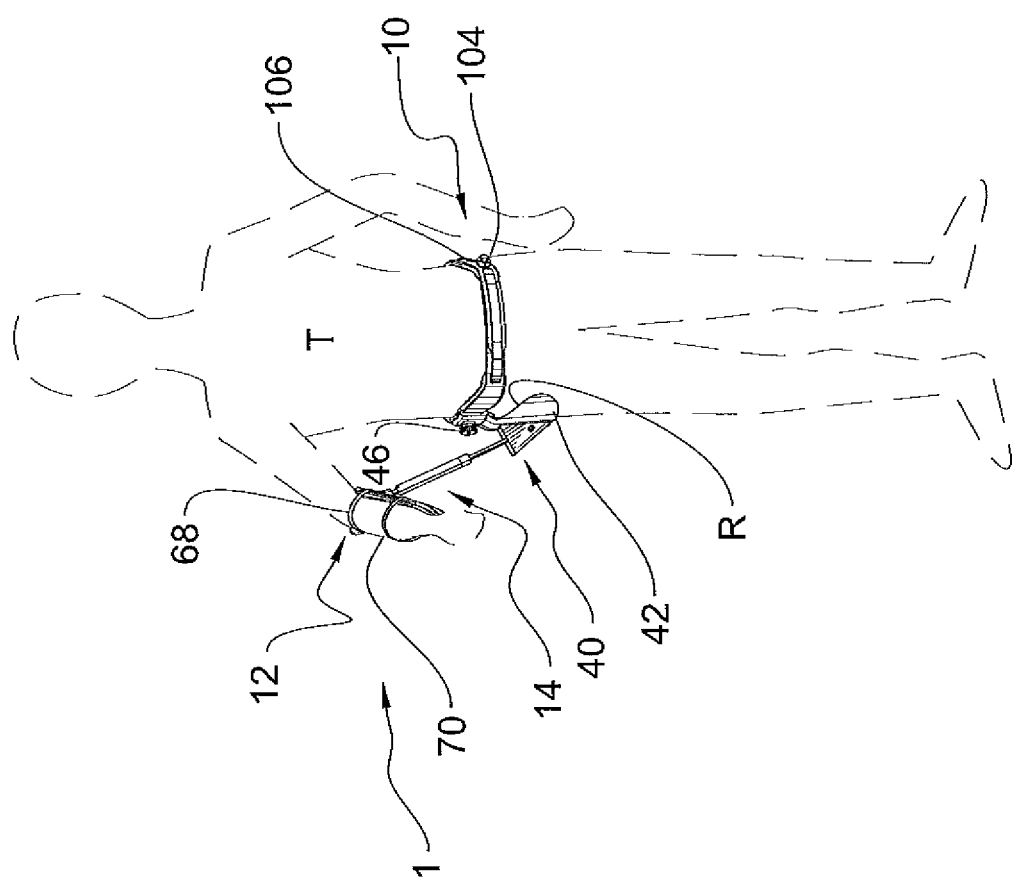
FIG. 1 is an elevational view of a patient in phantom lines, wearing a shoulder orthosis according to a preferred embodiment of the present invention, with the forearm splint in a partly retracted adduction condition.
Figure 2:
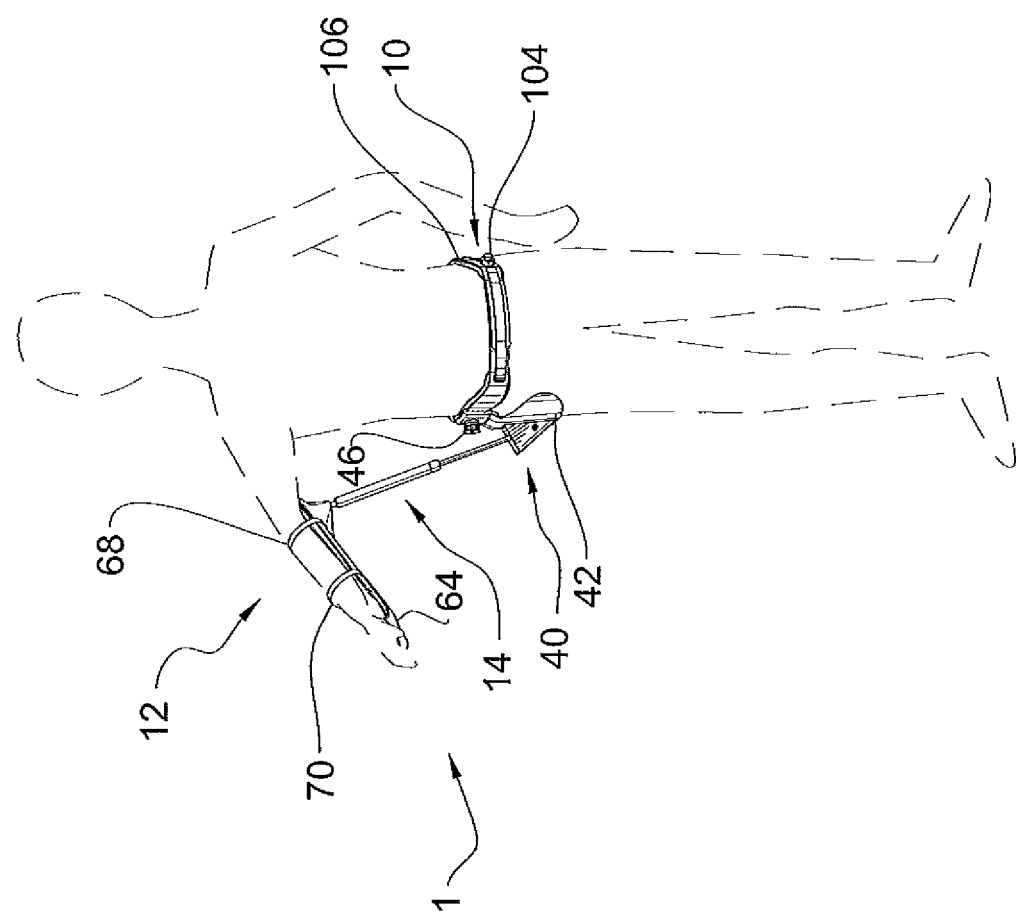
FIG. 2 is a view similar to FIG. 1, but with the forearm splint in an extended abduction condition.
Figure 3:
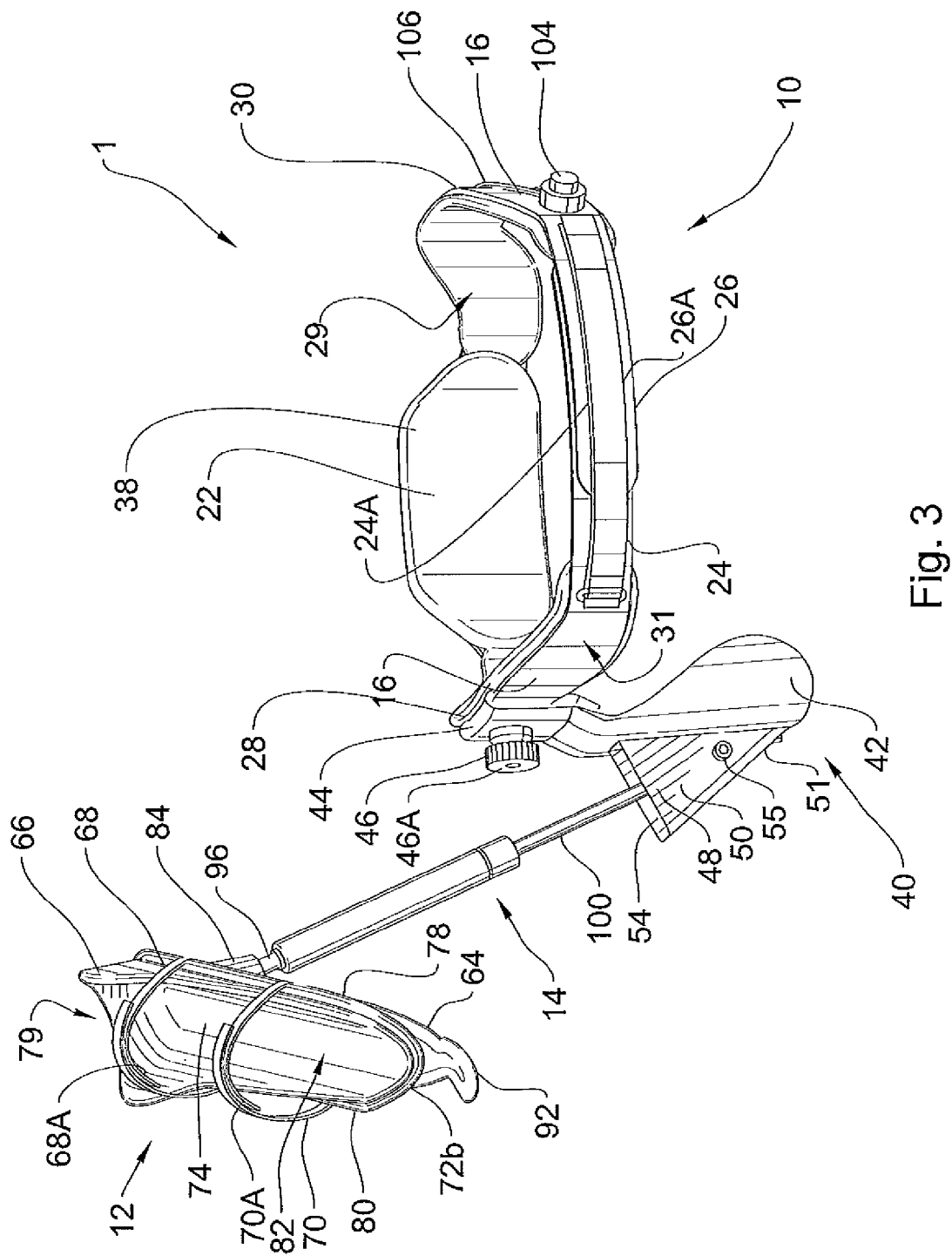
FIG. 3 is an enlarged front perspective view of the shoulder orthosis of FIG. 1 taken from a slightly elevated viewpoint.
Figure 4:
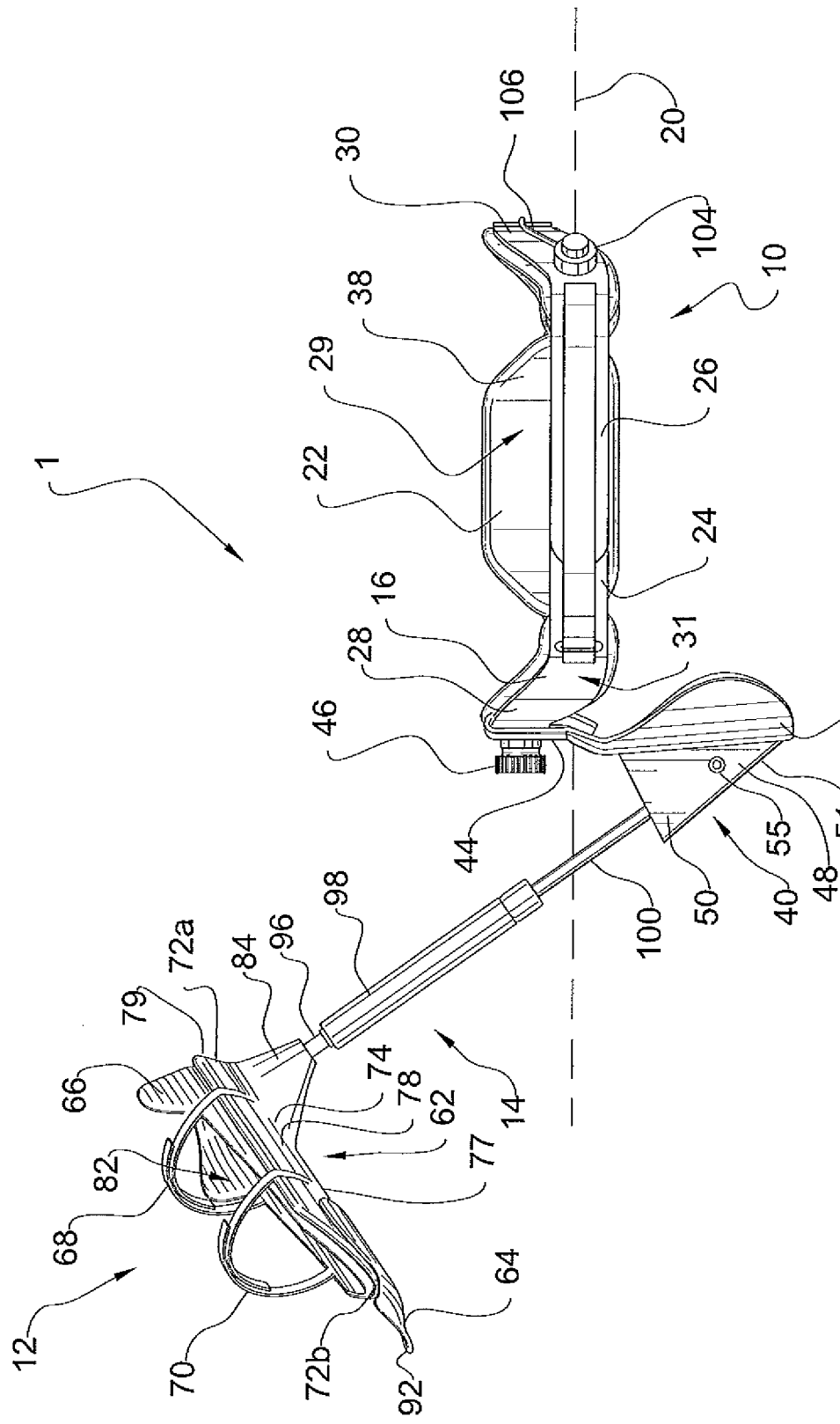
FIG. 4 is an elevational view of the shoulder orthosis of FIG. 1 showing the support member at a wide angle relative to the belt.
Figure 5:
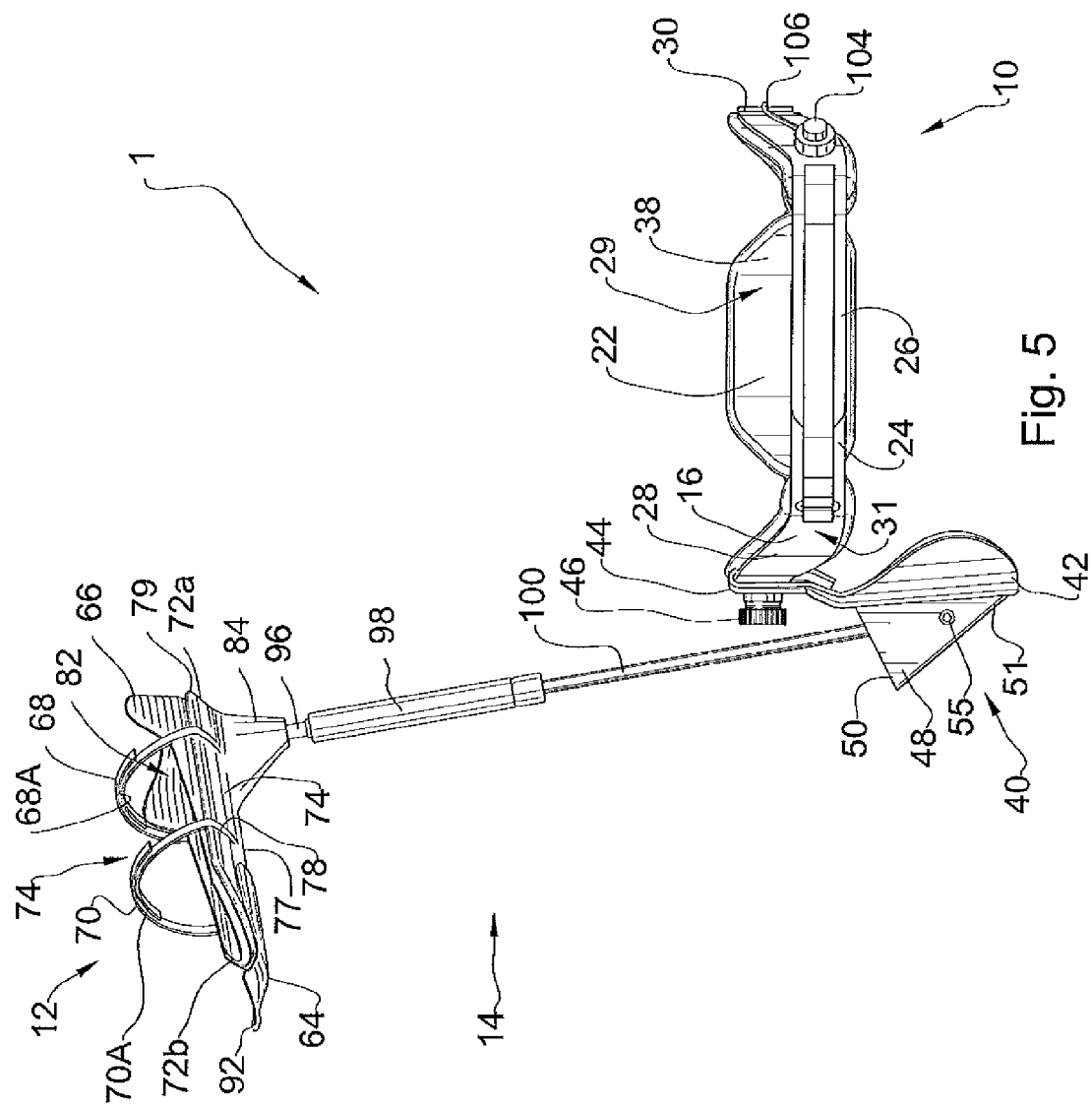
FIG. 5 is an enlarged view similar to FIG. 2, but without the patient's outline and showing the connector member in abduction.
Figure 6:
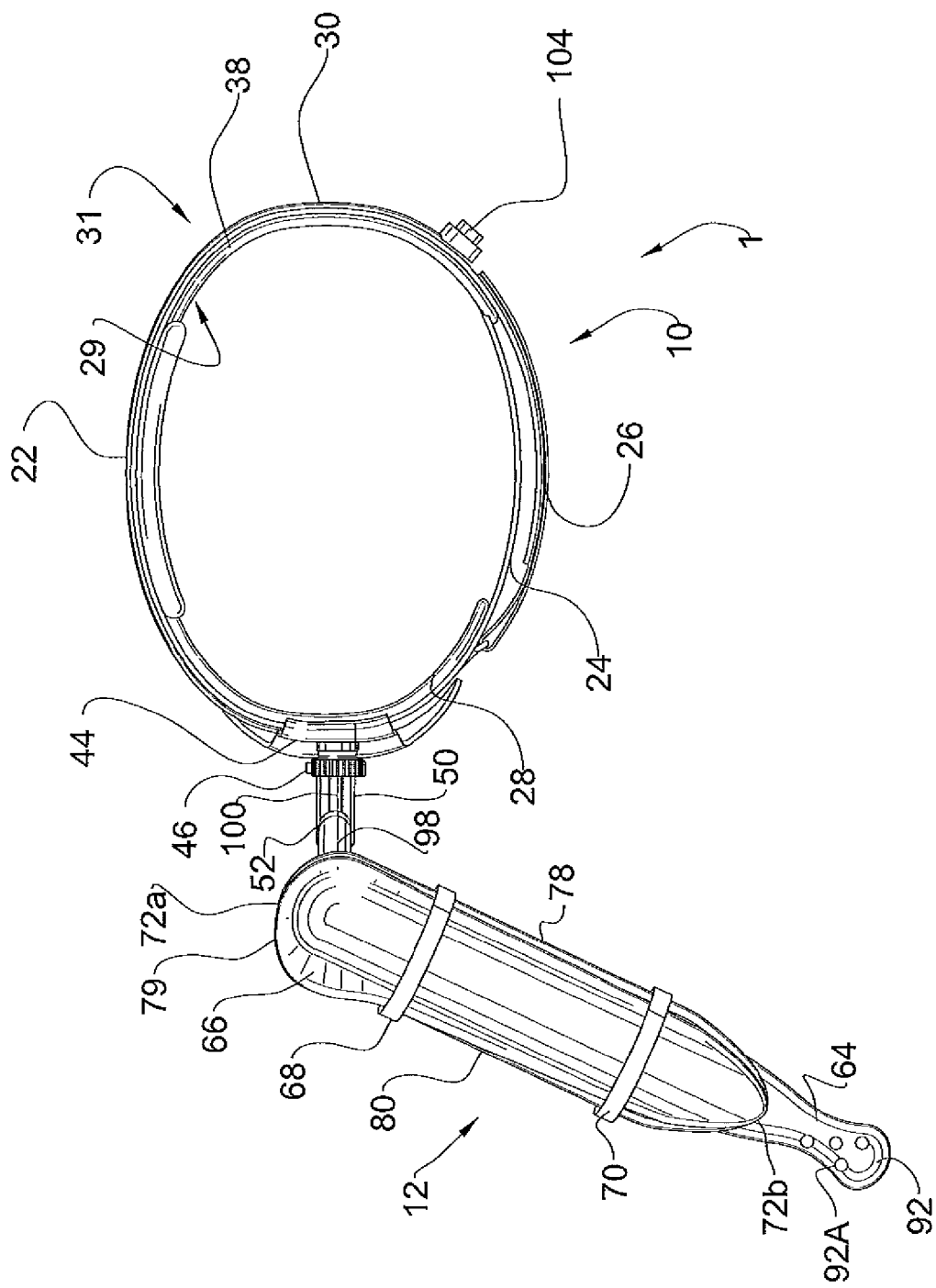
FIG. 6 is a top view of the shoulder orthosis of FIG. 5, with the forearm splint's free outer portion radially located away from the belt in extended condition of the patient's arm.
Figure 7:
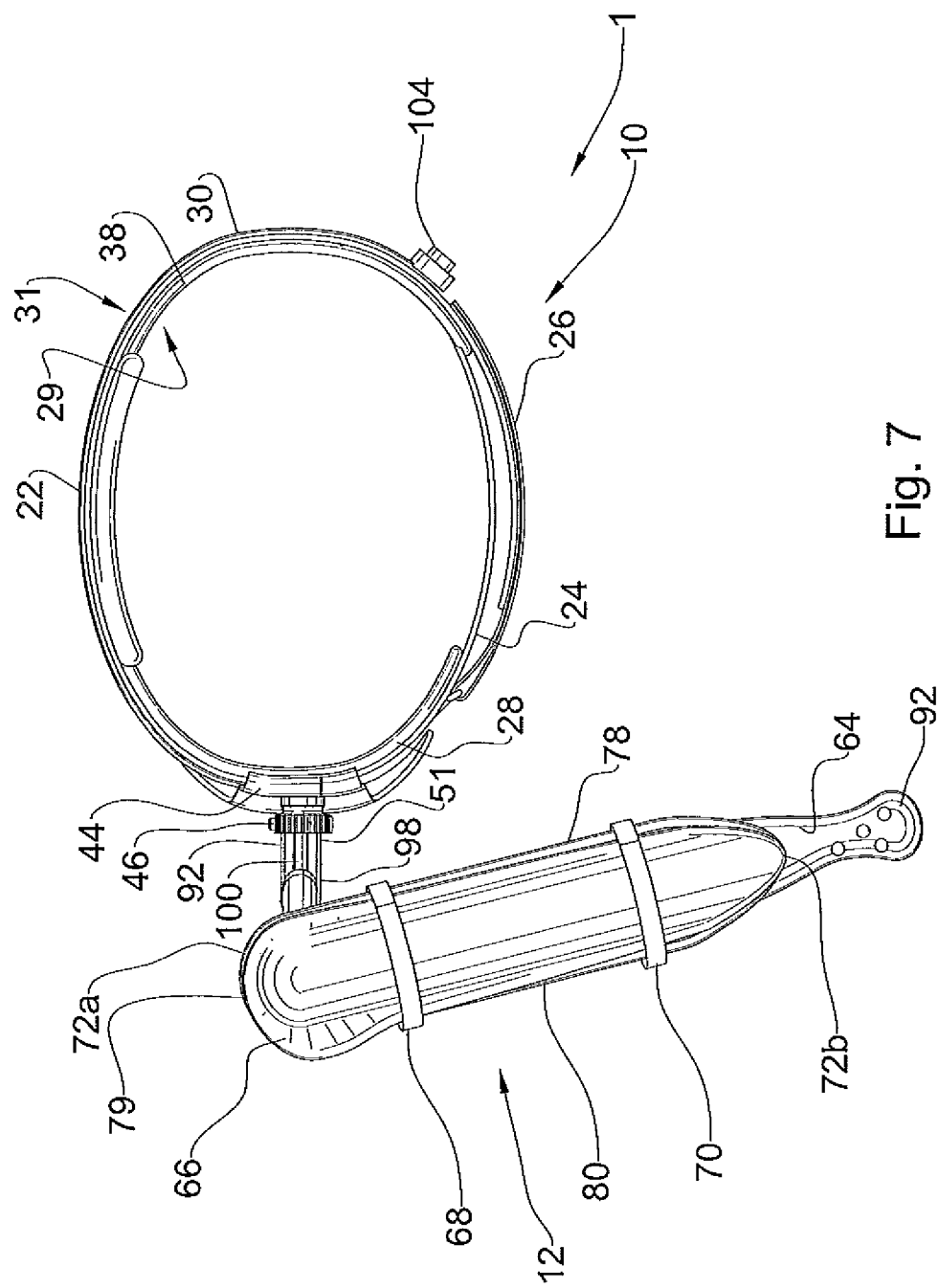
FIG. 7 is a view similar to FIG. 6, but with the forearm splint free outer portion pivoted radially closer towards the belt in flexed condition of the patient's arm about the same horizontal plane as in FIG. 6.
Figure 8:
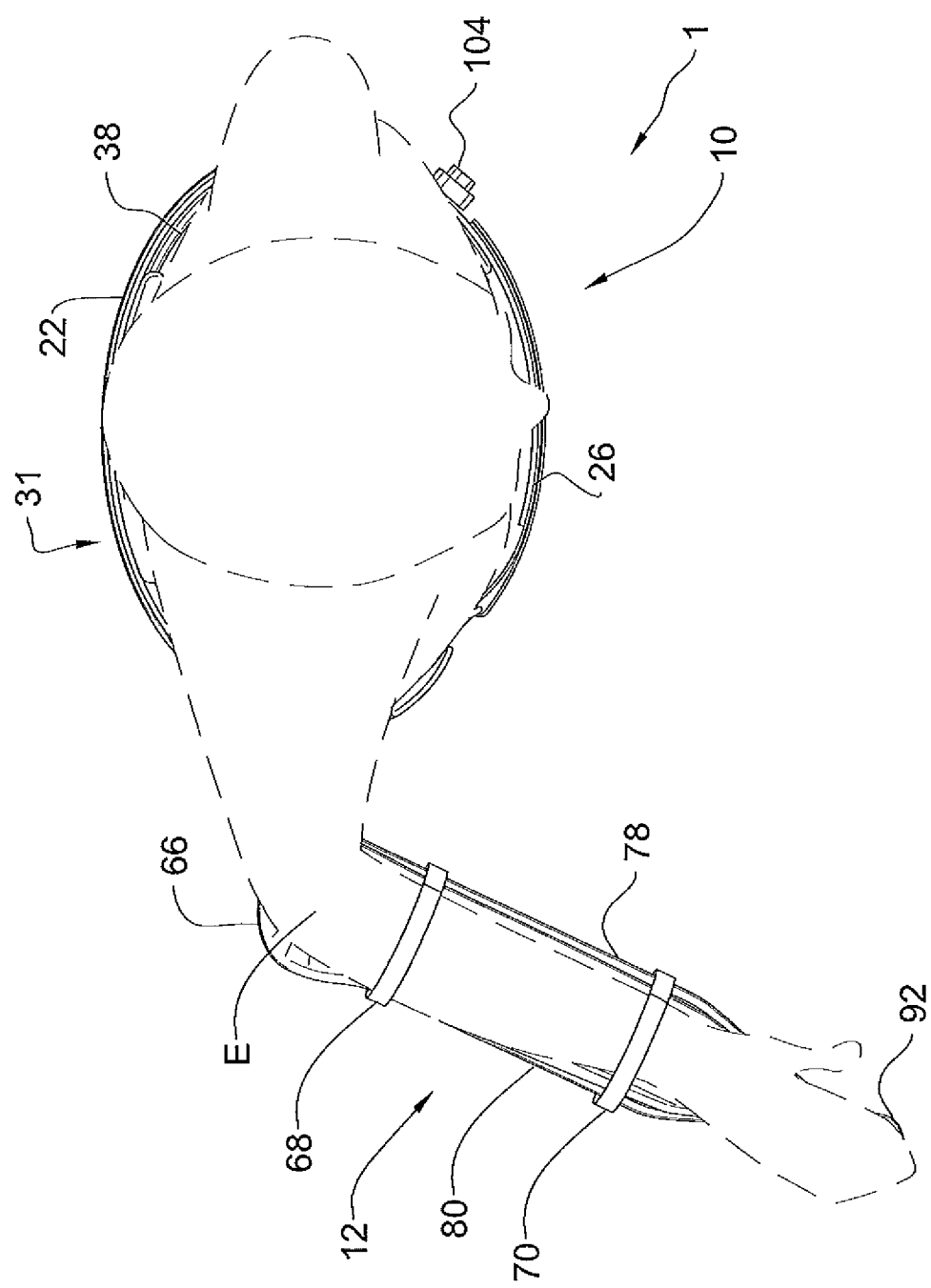
FIGS. 8 and 9 are views similar to FIGS. 6 and 7, respectively, but further showing a patient in phantom lines.
Figure 9:
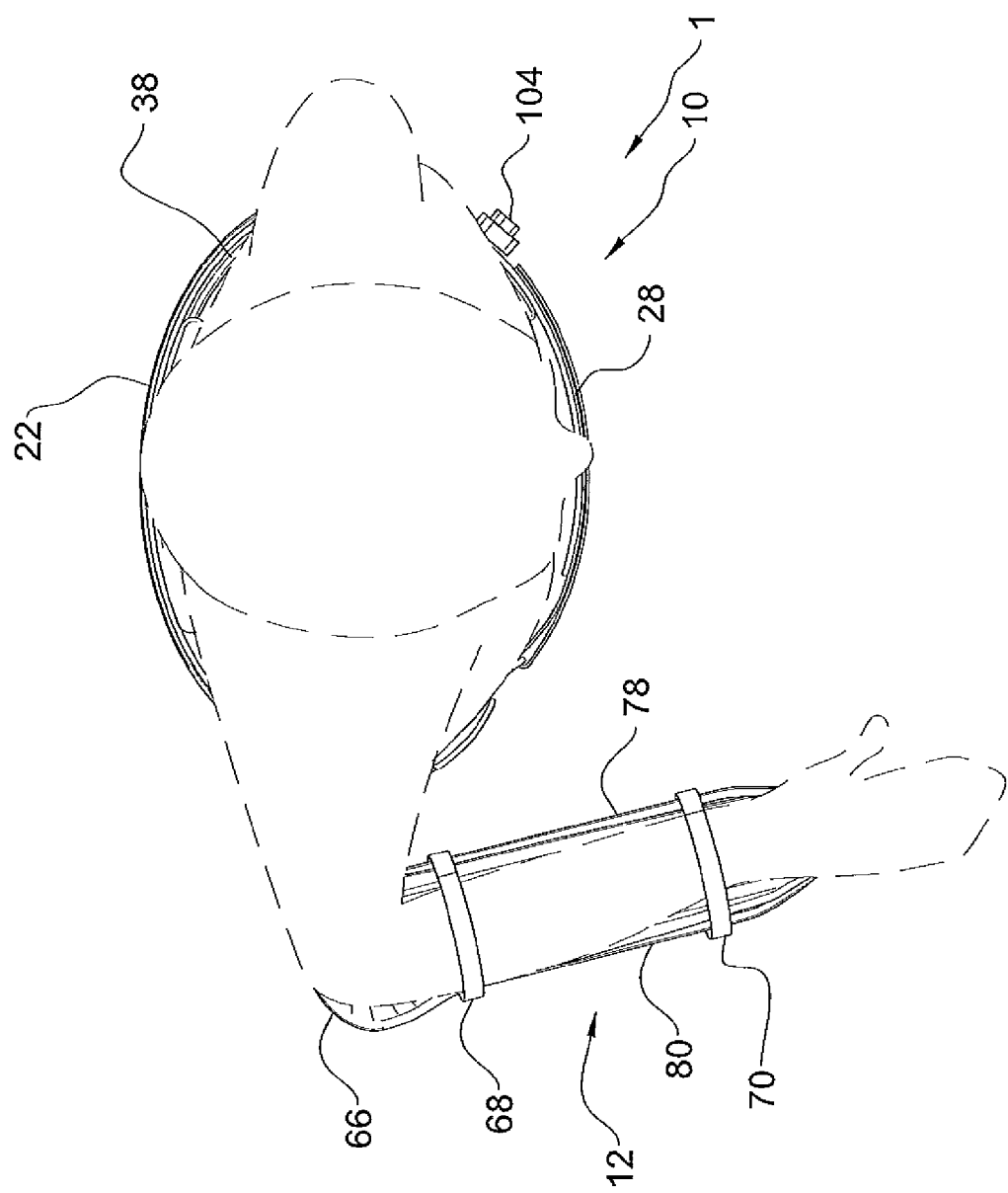
Figure 10:
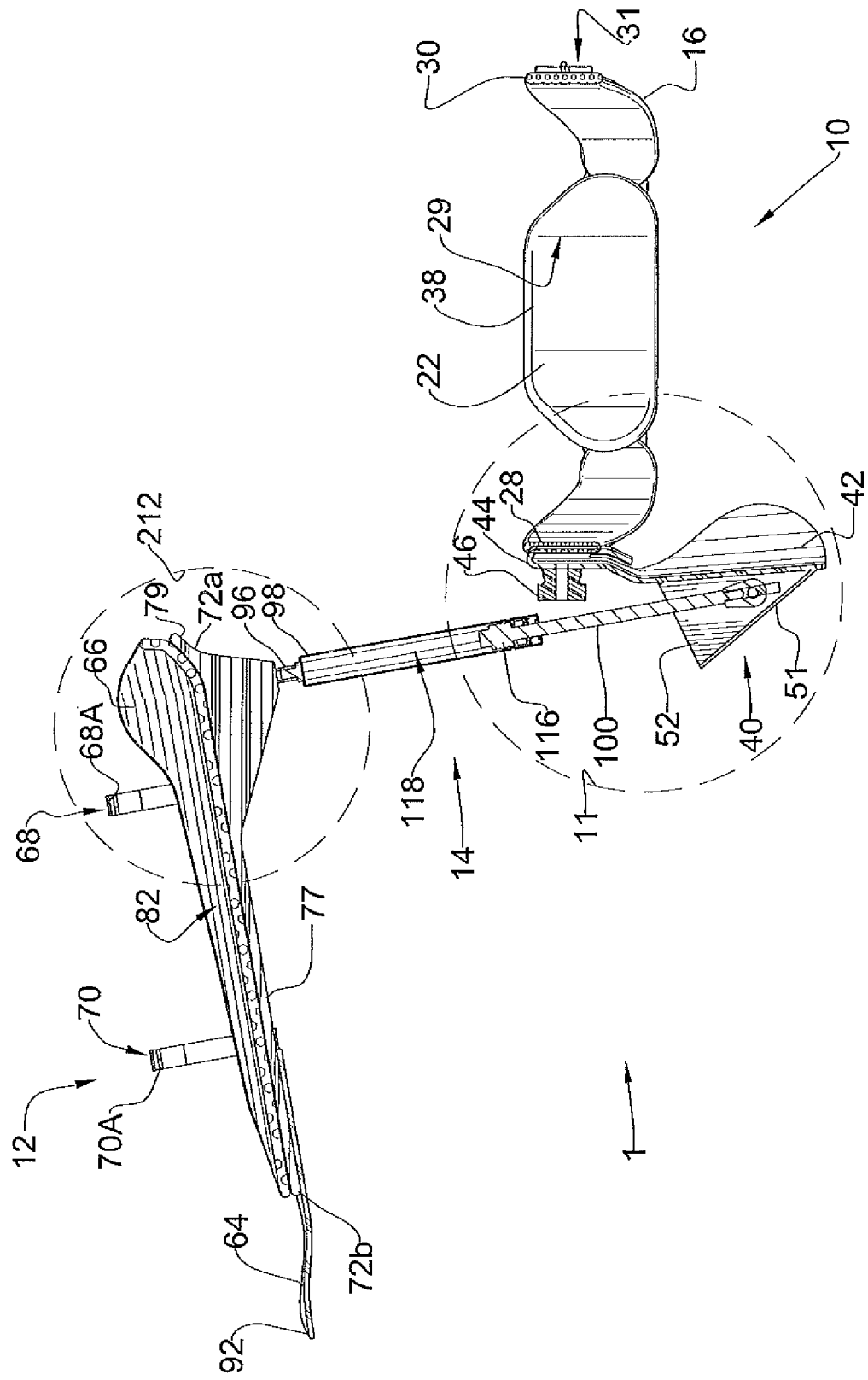
FIG. 10 is a view similar to FIG. 5 but with the piston rod being retracted in adduction condition and also showing a transversal cross-sectional view of the shoulder orthosis of FIG. 4 taken at midpoint between the front and the back of the belt and connector member.

Referring to accompanying FIGS. 1-14, there is shown a shoulder orthosis 1 according to a preferred embodiment of the present invention. Shoulder orthosis 1 comprises a waist harness 10, a forearm splint 12, and an extendible connector member 14 interconnecting harness 10 and splint 12.

Referring more specifically to FIGS. 3-5 and 10, waist harness 10 comprises a waist belt 16 having the general aspect of a strip made out of a fairly stiff yet extensible, semi-flexible and resilient material. Waist belt 16 is sized and shaped as to conformingly fit about the patient's waist adjustably to various waist lines. Waist belt 16 defines a baseline 20, a back section 22, first and second frontal sections 24, 26 each of which opposite back section 22, first and second hip sections 28, 30 opposite each other, an interior face 29 being the lateral section of waist belt 10 in contact with the patient, and an exterior face 31 opposite inner face 29. Hook and loop fastener band members 24A, 26A releasably adjustably interconnect waist flap sections 24, 26, respectively. Back section 22 is wider than the other sections of waist belt 16 and shaped to match the patient's back, to offer firm yet comfortable support. First and second hip sections 28, 30 deviate upwardly from baseline 20 so that they can rest fittingly over the patient hips, once again to provide firm yet comfortable support. Waist belt 16 can be flexed and stretched from a closed position, in which first and second frontal sections engage in partly overlapping fashion, and become releasably interlocked by adjustable hook and look fastener band members 24A, 26A, to an open position in which first and second frontal sections are spaced apart and clear one another, thus enabling the patient to either put belt 20 around its waist or remove same. Once around the patient waist, waist belt 20 can be stretched in place as to offer firm support.

Inner face 29 of waist belt 10 is lined with a belt padding 38 as to provide additional comfort when waist belt 10 is secured about the patient's waist. Belt padding 38 is preferably made out of a cushiony non-absorbent material, for example a 20 Shore hardness foam or a PODIALENE® foam, that can be kept in place even when shoulder orthosis 1 is used in wet conditions, as when the patient takes his/her shower. Waist belt 16, being fairly stiff and shaped as to retain the natural form of the waist, will help in maintaining waist harness 10 firmly in place once installed on the patient. This insures that the patient arms will stay put in the postoperative shoulder immobilization posture, and not move forward or backward, even after long hours of wearing orthosis 1.

Waist harness 10 also comprises a hip anchor 40 for receiving extendible connector member 14. Hip anchor 40 is symmetrical to and can be installed on either one of first and second hip sections 28, 30 of waist belt 16. Hip anchor 40 comprises a hip brace 42 that extends mostly below baseline 20, and is shaped and sized to fit the lateral registering trochanter portion R of the patient's hip, for stable tilt-free transfer thereto of the combined weight of the patient's arm, forearm splint 12 and extendible connector member 14 as explained in more details later on. Hip anchor 40 also comprises a belt dip 44 extending above baseline 20 and shaped to overlap fittingly either one of first and second hip sections 28, 30 of waist belt 16. Belt clip 44 is equipped with a belt lock button 46, which is a movable handle located over belt clip 44 that can be turned clockwise or counter clockwise to drive a set screw 46A respectively in and out of waist belt 16 as to respectively secure hip anchor 40 on waist belt 16 and release hip anchor 40 therefrom. Finally, hip anchor 40 comprises a yoke member stand 48 extending orthogonally from hip brace 42. Stand 48 comprises first and second triangular walls 50, 52 opposite each other and extending from hip brace 42, and a side wall 51 linking first and second walls 50, 52 on the side opposite to hip brace 42. First and second walls 50, 52, side wall 51 and hip brace 42 combine to form an open enclosure or pocket 54. A shaft 55 extends through walls 50, 52, thus traversing pocket 54, and is used to pivotally secure the lower end of support member 14 inside pocket 54, as explained in more details hereafter.

Still referring to FIGS. 3-5 and 10, forearm splint 12 comprises a forearm support 62, an outer end hand support 64, a forearm padding 66, and forearm fixation loop straps 68, 70. Forearm padding 66 may include for example an elastomeric compound, such as NEOPRENE®. The arcuate shape of forearm support 62 provides both a lateral support and anteroposterior support for the supported forearm. In this way, the supported arm will remain in place into the forearm support 62, even when the patient's body is laterally or rearwardly inclined. This will be particularly advantageous in the patient's everyday life, for example when the patient's lays on his/her bed, takes a bath/shower, eats a meal, . . . . Moreover, the symmetrical shape of the forearm support will readily adapt itself to any of the left or right arm, as the case may be.

The loop circumference of each strap band 68, 70, can be adjusted in length by providing hook and look fasteners 68A, 70A, at opposite ends thereof.

In one embodiment, forearm support 62 is made from an elongated piece made out of a rigid yet lightweight moldable material such as polyvinyl chloride (PVC), and defines opposite first inner end 72a and second outer end 72b. Forearm support 62 comprises an inner forearm bed 74, extending all the way between first and second ends 72a, 72b. Forearm bed 74 is generally arcuate or cross-sectionally U-shaped along its cross-section, and thus defines a base 77 and two lateral walls 78, 80 which all combine to form an inward forearm channel 82 suitable to receive the patient's forearm, with the patient elbow located near first end 72a and with the patient's wrist located near second end 72b of forearm support 62. Furthermore, lateral walls 78, 80 are joined together at first end 72a to form a transversely raised rounded back wall 79 in order to offer rear support for the patient's elbow, thus stabilizing the arm and preventing the elbow to accidently slide rearwardly when placed in forearm channel 82, while maintaining the elbow rotating axis coaxial with the rotating axis of the present orthosis, as will be explained hereinbelow. Forearm channel 82 remains open at second end 72b, allowing the patient's wrist and hand to extend outwardly therethrough. Forearm support 62 also comprises an upper support anchor 84, being a protrusion extending from forearm support 62 near first end 72a on the opposite side of forearm bed 74.

Figure 12:
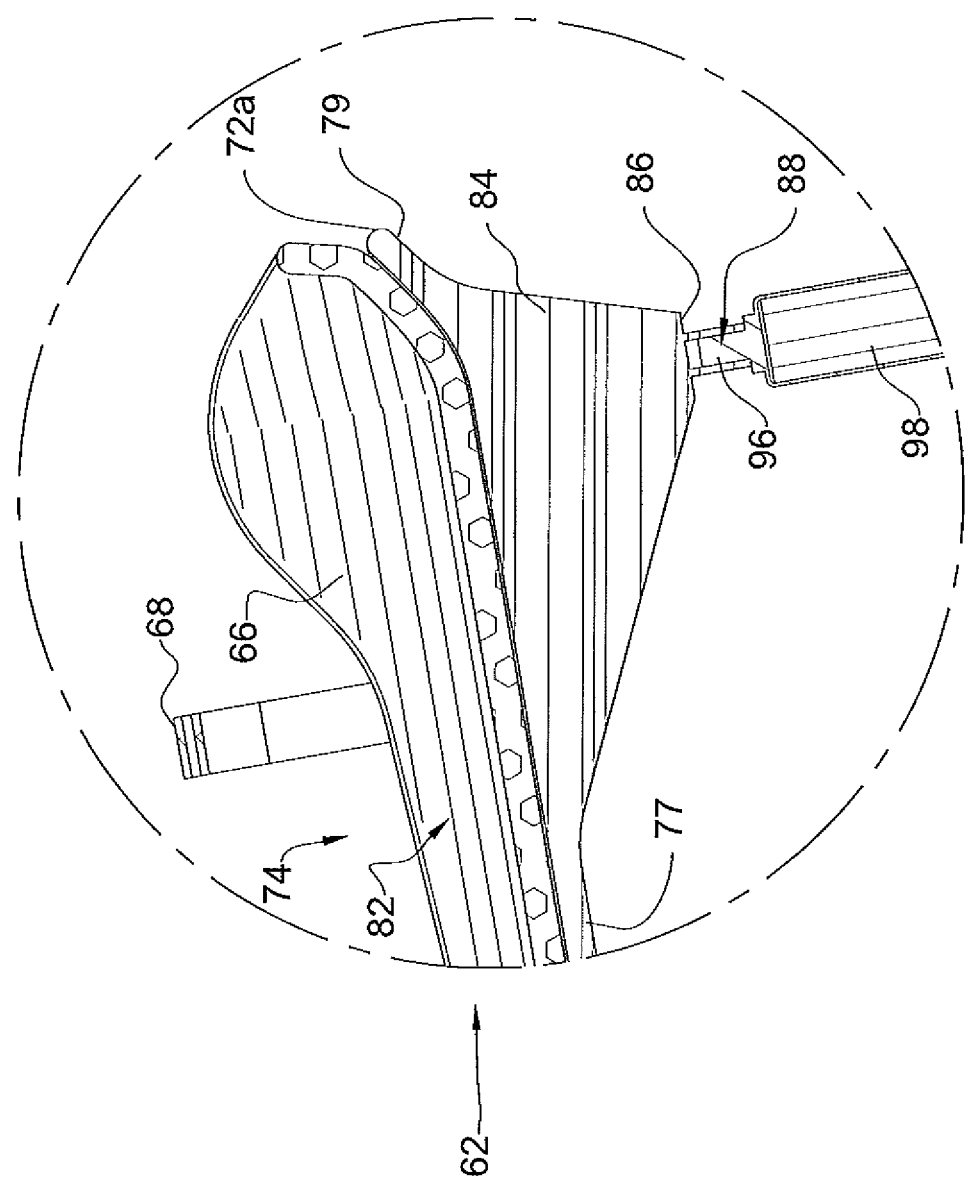
FIG. 12 is an enlarged view of the area circumscribed in circle 212 of FIG. 10, illustrating how the forearm splint is attached to the extendible connector member.

As shown in FIG. 12, upper support anchor 84 has the general aspect of a conical protrusion with a truncated base 86 opposite forearm bed 74. Truncated base 86 is pierced with a threaded bore hole 88 used to secure the upper end of support member 14, as explained in more details later on.

As shown in FIGS. 1-5 and 10, fixation straps 68, 70 are installed crosswise around forearm support 62 respectively near first and second ends 72a, 72b. Fixation straps 68, 70 are stretched around forearm support 62 and the patient's forearm so as to secure the latter in forearm channel 82. The combination of fixation straps 68, 70 together with lateral walls 78, 80 and back wall 79 enables the patient forearm to stay firmly in place and thus ensures that the shoulder is not being submitted to arm lifting loads as the patient leans back, forward, and sideways, or when the patient is lying in bed.

In another embodiment of the invention, fixation straps 68, 70 straps are integral parts of forearm padding 66, each one having a fixed end on one side of forearm padding 66, and a loose end that is first stretched over the patient's forearm and then under the splint, to be finally attached over itself using fasteners such as hook and loop fastener strips 68A, 70A.

Forearm support 62 is fined with forearm padding 66 so as to increase comfort for the patient's forearm. Forearm padding 66 is shaped as to match forearm bed 74, extending slightly above lateral walls 78, 80, and more importantly near back wall 79, which increases the overall tilt-free stability of the patient's forearm in forearm bed 74. Said forearm padding 66 is preferably made out of a cushiony non-absorbent material that can be kept in place when shoulder orthosis 1 is used in wet conditions. Finally forearm padding 66 being opened upwardly ensures natural ventilation as to maintain a comfortable temperature of the forearm.

Still referring to FIGS. 3-5 and 10, hand support 64 is fixed to forearm channel 82 on the opposite side of forearm bed 74 near second end 72b, and extends lengthwise outwardly therefrom. Hand support 64 is an elongated plate defining a fixed end shaped to overlap forearm 64 on the attachment location, and a loose end opposite fixed end, being a palm rest tab 92. Hand support 64 is made from a stiff yet extensible material. Palm rest tab 92 can thus be adjustably extended to accommodate patients with various arm lengths. A semiflexible connection of palm rest 92 with hand support 64 allows palm rest tab 92 to twist sideways, e.g. by up to 20° on each side, to accommodate supination and pronation motions occurring when the patient's moves his arm. Palm rest tab 92 is slightly transversely inclined relative to the plane of base 77 of forearm support 62 as to maintain the patient's wrist in slight extension. This thereby reduces the pressure in the carpal tunnel as to avoid adverse side effects related to carpal tunnel syndrome. Palm rest tab 92 may be pierced with a number of aeration bores 92A to let air flow therethrough, thus reducing discomfort caused by sweat.

Figure 13:
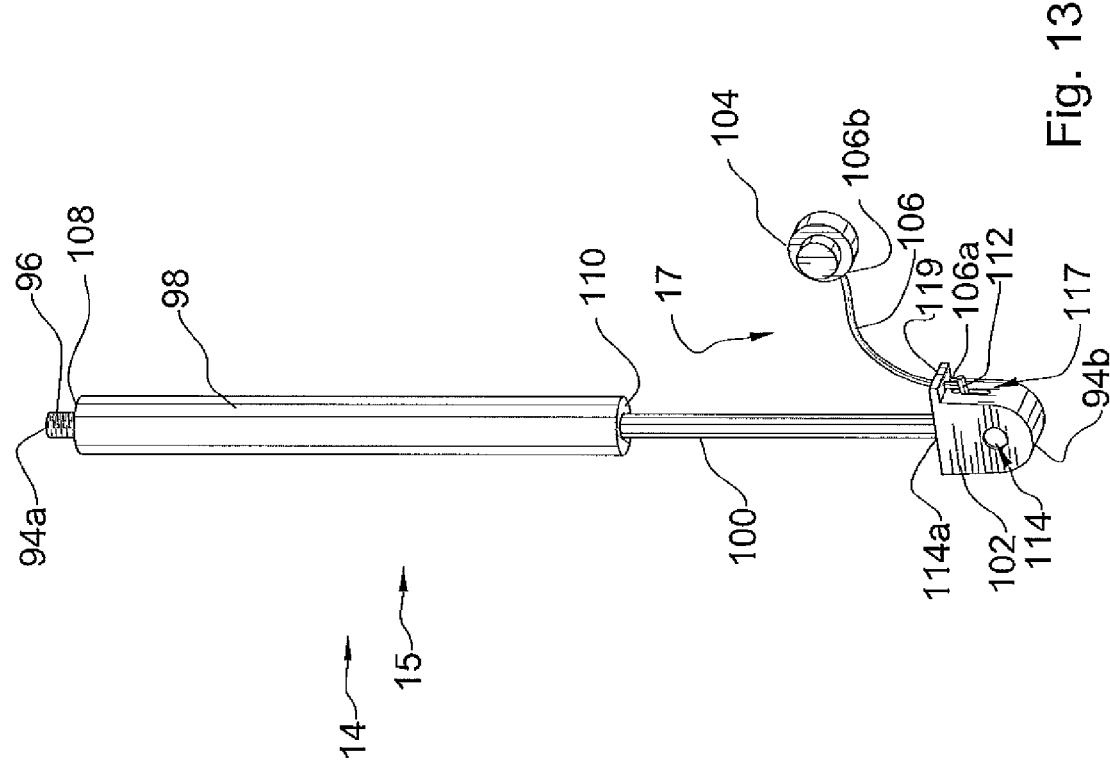
FIG. 13 is a cut away enlarged perspective view of the piston and cylinder actuator of the shoulder orthosis of FIG. 4, showing how the piston yoke member is operatively connected to a remote control knob.
Figure 14:
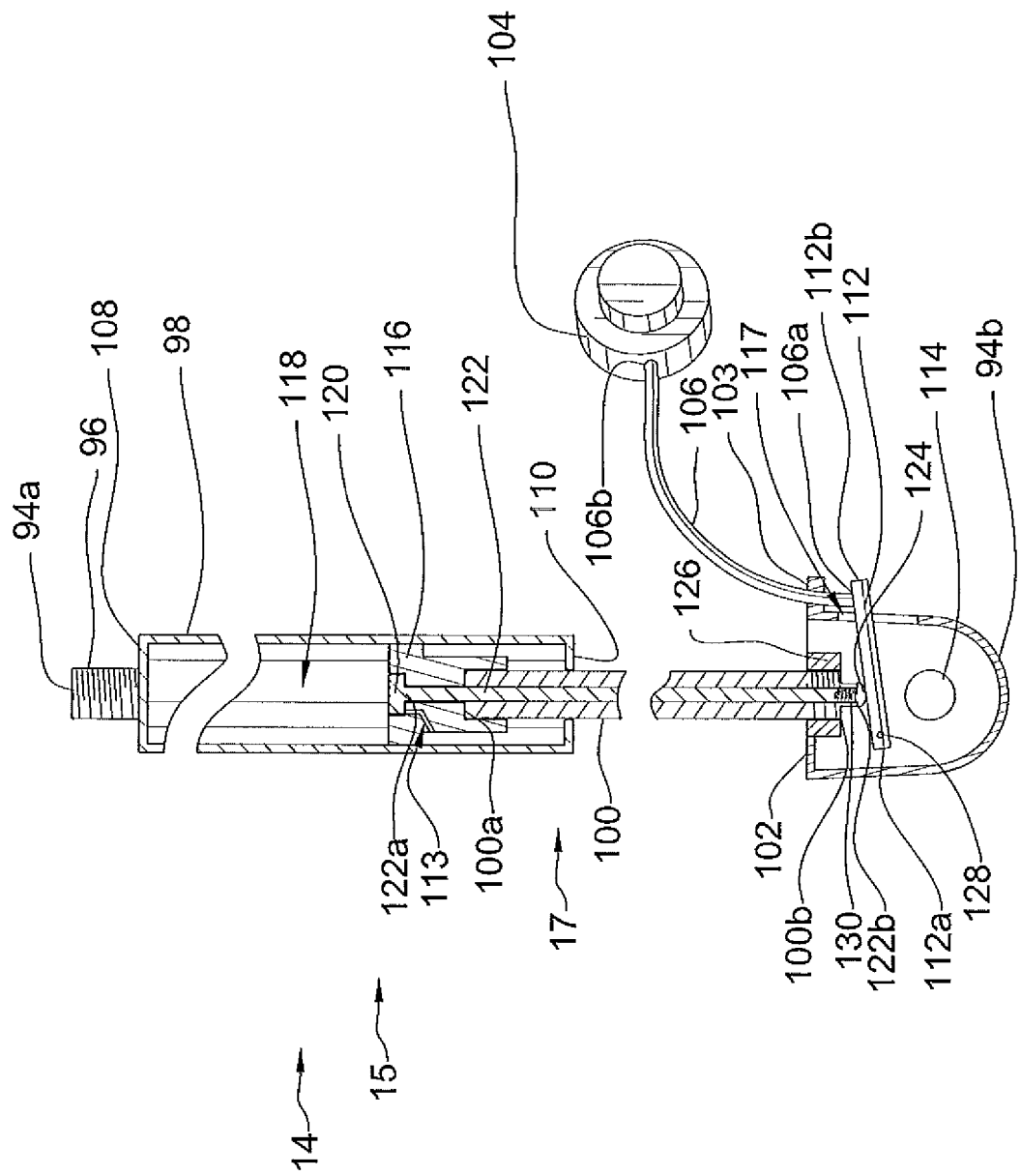
FIG. 14 is an enlarged partly broken sectional view of the components of FIG. 13.

Referring now to FIGS. 13 and 14, there is shown a support member 14 being a gas spring with elastic locking as can be commonly found in the industry, such as the "Bloc-O-Lift with Elastic Locking" from the "Stabilus Inc." company. Elastic locking offers comfortable damping when a force is applied on both ends of the hydraulic cylinder and is thus best suited for human interaction. Connector member 14 comprises a generally elongated gas spring 15 extending from a first cylinder end 94a to a second piston end 94b, opposite first end 94a. Starting from first end 94a, gas spring 15 comprises in turn a cap screw 96, a cylinder barrel 98, a piston rod 100 and an outer piston head yoke base 102. Barrel 98 is an elongated hollow cylinder comprising a pressure chamber 118, a barrel cap 108 on one end, and a barrel head 110 on opposite end. Barrel head 110 is pierced in its center as to allow piston rod 100 to move lenghtwisely therethrough. Piston rod 100 also rotates freely relative to barrel 98. Piston rod 100 comprises a first inner end 100a fixed to an inner piston head 116 mounted inside barrel 98, and a second opposite outer threaded end 100b fixed to yoke base 102 using a screw bolt 126.

Figure 11:
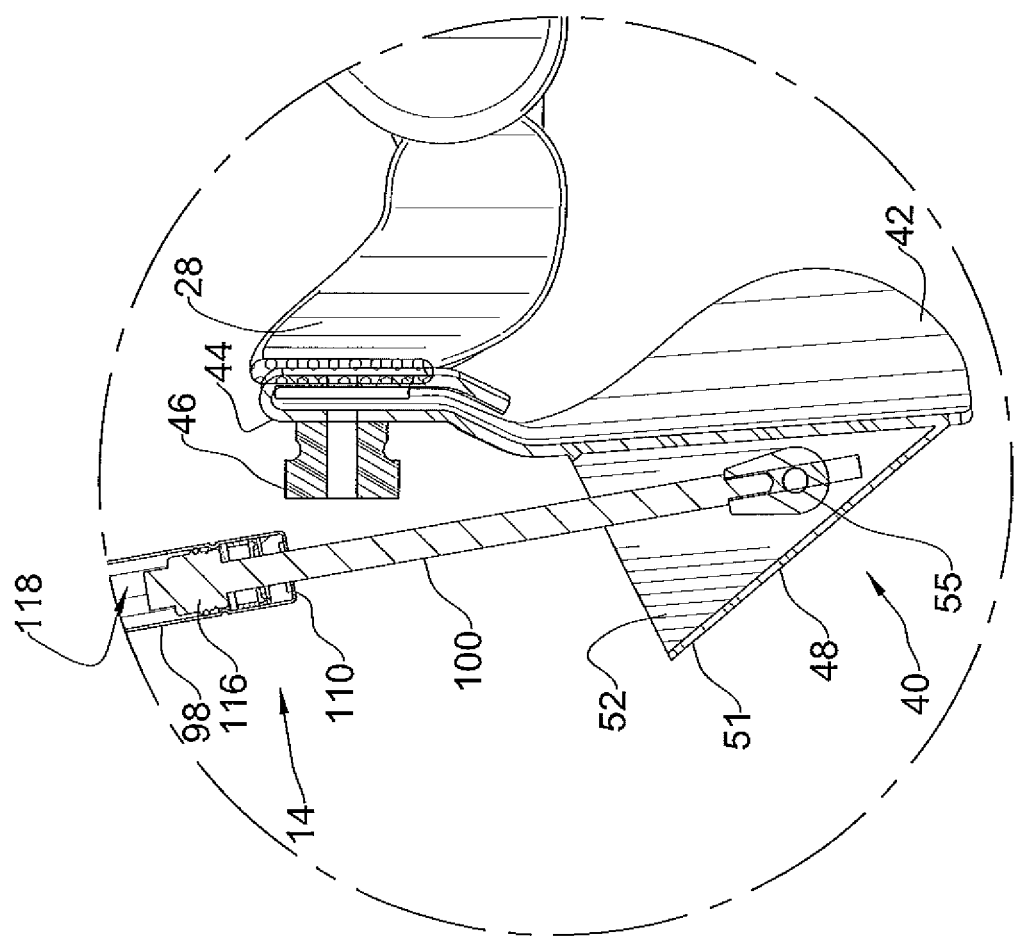
FIG. 11 is an enlarged view of the area circumscribed in circle 11 of FIG. 10, illustrating how the hip anchor attaches to both connector member and to the belt.

As shown in FIGS. 10-14, first threaded end portion 94a of cylinder 98 is fixed to upper anchor 84 of forearm splint 12 by inserting and screwing cap screw 96 into bore hole 88. Cap screw 96 is a simple bolt screw welded on atop barrel cap 108. As illustrated in FIG. 11, second end 94b of support member 14 is pivotally mounted to stand 48 of hip anchor 40 about pivot shaft 55, which passes through a fixation hole 114 in base 102.

Connector member 14 also comprises a manual (hand or foot activated) actuation mechanism 17 enabling to put gas spring 15 in either a locked state, in which the condition of piston 116 is fixed relative to barrel 98, or in an unlocked state, in which piston 116 can extend/retract in barrel 98 between barrel cap 108 and barrel head 110 in order to either accumulate pressure in or release pressure from pressure chamber 118. Actuation mechanism 17 comprises an actuator rod 122, which is an elongated shaft passing through piston rod 100 and piston 116, through both of which it can move longitudinally. Actuator rod 122 defines a first end 122a connected to an actuator valve 120 atop piston 116, and a second end 122b connected to an actuator tappet 124 inside yoke base 102. Piston 116 comprises a vent 113 allowing gas exchange between the two sections of pressure chamber 118 on each side of piston 116 when valve 120 is opened. Second end 122b of actuator rod 122 extends longitudinally beyond second end 100a of piston rod 100, thus leaving space between tappet 124 and piston rod 100 for spring loaded actuator coil 130, which is placed therebetween and around actuator rod 122. Actuator mechanism 17 also comprises a lever 112, defining a first end portion 112a, and a second end portion 112b opposite first end 112a. Lever 112 is pivotally carried by base 102 using a transverse pivotal shaft 128 near its first end 112a. Second end portion 112b of lever 112 extends throughout and beyond of one side of base 102 through a lever opening 117 made in base 102, thereby allowing second end portion 112b of lever 112 to translate during pivotal action about shaft 128 of lever 112. Lever 112 is placed as to lean against actuator tappet 124 in order to push or be pushed by the latter. Actuator mechanism 17 also comprises a Bowden cable 106 passing through a Bowden cable guide 103 fixed to base 102 spacedly over lever 106. Bowden cable 106 defines a first end 106a connected to lever 112 near second end portion 112b, and at a second end 106b connected to an actuator button 104 at a distance from cylinder 15. Actuator button 104 may be fixed on either one of waist belt hip sections 28, 30 being opposite to hip anchor 40, with Bowden cable 106 running for example along back section 22 of waist harness 10. Actuator button 104 is thus easily accessible manually by the patient on his/her uninjured side, for operation of support member 14.

When button 104 is pressed, Bowden cable 106 exerts a pull force on lever 112, which in turn pushes actuator tappet 124, actuator rod 122 and actuator valve 120. This results in coil 130 being compressed and actuation valve 120 being lifted above piston 116. Vent 133 is thus opened and gas spring 15 is put in its unlocked state. When button 104 is released, so is the pull force of Bowden cable 106 on lever 112. Coil 130 being resilient can then expand to regain its initial form, thereby pushing lever 106 away from Bowden cable guide 117, and thereby closing actuator valve 120 through the intermediary action of actuator rod 122. Vent 113 is thus closed and gas spring 15 returns to its locked state.

When gas spring 15 is in the locked state, it acts as a simple support structure with damping effect. When gas spring 15 is in the unlocked state, pressure can be accumulated inside pressure chamber 118 by retracting piston rod 100 into cylinder 98, i.e. by applying an inward force between first and second ends 94a, 94b of gas spring 15, thereby axially moving piston 116 from a first condition closest to barrel head 110 where gas spring 15 is said to be expanded, to a second condition closest to barrel cap 108 where gas spring 15 is said to be a fully retracted. Gas spring 15 is said to be a partially retracted when piston 116 is located anywhere in between said first and second positions. When gas spring 15 is brought to its partially or fully retracted condition, e.g. upon adduction movement bringing the arm closer to the sagittal plane of the patient's body, when the patient's arm applies a retracting load on support member 14 mainly with his/her healthy pectoralis major and latissimus doris muscle, the pressure accumulated in pressure chamber 118 tends to return gas spring 15 to its expanded state by pushing piston 116 to its first position closest to barrel head 110. So whenever the inward force applied between first and second ends 94a, 94b of gas spring 15 is smaller than the outward force exerted on piston 116 by the pressure accumulated in pressure chamber 118, gas spring 15 naturally expands towards its expanded state, wherein abduction movement brings the arm away from the sagittal plane of the patient's body.

In another embodiment of the present invention, gas spring 15 is replaced by a mechanical coil spring with similar properties. Other types of damper means are not excluded from the scope of the present invention.

In use, shoulder orthosis 1 comes preassembled with connector member 14 already fixed to forearm splint 12 and hip anchor 40, as explained previously. Connector member 14 is then fixed to either one of first and second hip sections 28, 30 of waist belt 16 located on the side of the patient's injured elbow using belt lock button 46. Actuator button 104 is then placed on either one of hip sections 28, 30 on the opposite side of hip anchor 40, with Bowden cable 106 running along back section 22. Waist belt 16 is then placed about the patient's waist, with hip sections 28, 30 resting on the top of the patient's hips, with hip brace 42 along the side of the patient's hip, and with back section 22 resting on the patient's back, first and second frontal sections 24, 26 are then stretched and overlapped to secure waist belt 16 in place using male and female hook and loop fastener strips 24A, 26A. The length of forearm gas spring 15 is then adjusted at the height best suited for the patient's injured condition, i.e. in abduction condition as prescribed by the orthopedic surgeon. This is done by unlocking gas spring 15 with actuator button 104, then extending or compressing gas spring 15 to get forearm splint 12 at the desired height, and by finally releasing actuator button 104 for locking gas spring 15, thereby locking forearm splint at the desired abduction height. The patient's forearm is then placed in forearm channel 82, with his/her elbow leaning on back wall 79, and with his/her hand extending over hand support 64. The patient's forearm is finally secured in forearm splint 12 using the two forearm fixation straps 68, 70, and associated hook and look fasteners 68A, 70A, and palm rest tab 92 is adjusted according to the patient's forearm length, so that his/her hand can rest comfortably thereon. As the muscle healing progresses, after a number of days or a few weeks of rehabilitation, the prescribed height of forearm splint can be adjusted in adduction motion after validation from the orthopaedic surgeon. This is done using the same method as for the initial height adjustment.

Once in place on the patient, orthosis 1 enables the patient to perform two types of movement while preventing arm lifting abduction loads being applied on the shoulder injured muscles. The first enabled movement is the elbow extension/flexion in horizontal plane during which the patient can move his forearm radially back and forth relative to his/her torso T while his elbow remains in place, as suggested in FIGS. 6-9. During this forearm flexion/extension motion, the pivotal axis of the patient's elbow E remains coaxial with the lengthwise axis of the piston rod and cylinder assembly 98, 100. This type of movement is convenient for exercising the patient's arm by maintaining tonus of remaining healthy muscles and to eliminate numbness in the arm cause by a prolonged stabilisation. It also enables the patient to perform certain daily activities such as eating, reading, donning a coat or drawing bedsheets while in bed.

Gas spring 15 ensures a stable and natural flexion of the forearm by being placed directly underneath the patient's elbow. The rotation movement is enabled by barrel 98 which can turn axially relative to piston rod 100. Also, this flexion of the arm can induce supination and pronation, which naturally occur as the forearm is respectively brought radially towards and away from the torso T. Flexible palm rest tab 92 ensures that the hand always rests in a comfortable position as it is respectively turned face up and face down.

The second enabled movement by the present orthosis is the flexion of the shoulder for exercising the uninjured adductor muscles of the arm. To exercise these uninjured adductor muscles of the arm, the patient presses manually with the healthy arm on actuator 104 and maintains it pressed in order to unlock gas spring 15. This movement is enabled after the orthopedic surgeon has lowered the arm in such a way that the gas spring has completely retracted. Gas spring 15 then naturally expands towards its expanded state, as explained previously. This lifts the patient arms in power assisted abduction movement without imparting muscular loads on the injured patient abductor muscles from a lowered position, as pictured in FIG. 1, to a raised position, as pictured in FIG. 2. Once the patient arm reaches the recommended maximal height for the exercise, relative to the patient's sagittal plane, the patient uses his adductor muscles to lower his arm against the bias of gas spring 15, thereby stopping the expansion of gas spring 15 and compressing gas spring 15 until his/her arm reaches the minimal height recommended for the exercise. At that point, the patient can continue exercising by relaxing its adductor muscles. Gas spring 15 then expands once again and the patient can repeat the exercising steps presented previously. When the patient is done with exercising, he simply releases actuator button 104 to lock gas spring 15 when his/her arm reaches the lowest position. This flexion of the shoulder is made comfortable to the patient by the damping effect of gas spring 15, and by flexible mounting of palm rest tab 92 which can accommodate for natural supination and pronation of the forearm also induced by this type of movement. This flexion of the shoulder implies lateral swinging movement of the elbow towards and away the patient's body induced as the arm is respectively brought in adduction or abduction. This lateral movement of the elbow is enabled by gas spring 15, which is rotatably fixed to stand 48 by shaft 55, enabling first end 94a of connector member 14 to move towards and away the patient's torso T, and thereby adjustably accommodating this type of movement. Furthermore, as the arm is raised and lowered, a slight axial rotation is induced in barrel 98 of gas spring 15. This axial rotation is once again enabled by the fact that barrel 98 can rotate axially relative to piston 100.

Again, the present orthosis enables the patient to bring his forearm towards and away his body while keeping his arm generally horizontal and at a constant angle relative to his body. This type of movement can be very useful to the patient, enabling him to perform daily tasks while healing, such as eating or reading.

In one embodiment, during a first step of the first three weeks or so of initial healing while the patient wears the present orthosis 1, the patient's arm is immobilized in the abduction position, with the gas spring 15 in extended limit condition, or alternately in an intermediate non limit extended condition, with the piston being locked, while the Bowden cable 106 could be removed or simply disconnected. The patient should not lower his/her arm beyond the immobilization position thereof. Only the flexion/extension of the elbow should be allowed, with no adduction/abduction. The orthopedic surgeon may recommend to bring the patient's arm closer to the patient's body. Afterwards, during a second step of the fourth to sixth week or so of healing, the arm will be immobilized in the adduction position, with the gas spring 15 being closed, to enable patient's exercising, the piston 116 will be temporarily unlocked. In the immobilization position, the piston 100 rod is engaged into the cylinder 98 (adduction) and it is when the patient wants to exercise that the patient's arm is lifted by the extension of the piston rod 100 and that the adductor muscles (latissimus dorsi and pectoralis major) are used to draw the patient's arm in immobilized position. When the muscle injury is minor, and upon recommendation from the orthopedic surgeon, step 1 corresponding to the above-noted first three weeks of recommended protocol may be ignored, so that the healing process would carry on directly to above noted step 2 without needing to go through step 1. In this latter case, the length of the piston rod 100 when retracted must correspond to the immobilization abduction angle determined by the orthopedic surgeon to be appropriate considering the nature of the injury. During exercising, the arm will be lifted in abduction. It is thus understood that the patient exercising activities may well go in abduction beyond the immobilization position under the bias of the gas spring 15, passively for and without stretching the injured muscle, but should not go beyond this lower threshold. It is therefore understood that the orthosis immobilization position is the orthosis position with the piston rod 100 being retracted. Therefore, it is only during above noted phase 2 of use of the orthosis 1 that the adductor muscles are active by air compression in the cylinder 98.

It is understood that the mechanical features of the arm support member 14 should be custom adjusted for each different patient, as a function of his/her anthropometric parameters, including:
  a) length of arm;
  b) length of body trunk;
  c) weight of injured arm;
  d) type of muscle injury.

The optimal post operative shoulder immobilization abduction posture for rotator cuff tears involving supraspinatus (and possibly infraspinatus) muscles in accordance with the present invention, will be according to the orthopaedic surgeon evaluation.

The invention claimed is:

1. Shoulder orthosis for long term support of a patient's arm in postoperative shoulder immobilization abduction posture for injured rotator cuff muscle tear, said orthosis comprising:
  a) a waist belt member, releasably adjustably attachable to the patient's waist line;
  b) an arm splint, defining opposite outer and inner end portions, and releasably adjustably attachable to the patient's arm;
  c) an extendible connector member, spacedly interconnecting a support section of said belt member to said splint inner end portion and defining a lengthwise axis thereof, wherein said splint is movable in translation between a fully extended abduction first limit condition and a retracted adduction second limit condition, angularly relative to the patient's torso;
  d) a damper means for cooperating with said connector member in biasing said splint away from said belt member, wherein said damper means enables cyclical back and forth extension/retraction of said extendible connector member between said first and second limit conditions thereof;
  e) a locking means for releasably locking said extendible connector member at a selected condition thereof against the biasing force of said damper means; and
  f) a splint swing motion compensating means for providing transverse play of said connector member transversely of said lengthwise axis thereof, to accommodate inward rotation of the patient's arm naturally induced as the patient's arm is raised away from the patient's torso;
wherein said orthosis enables cyclical exercising of the patient's arm healthy adductor muscles while minimising contraction of the injured muscles in the rotator cuff.

2. A shoulder orthosis as in claim 1, wherein said swing motion compensating means consists of a rotating member, integral to said connector member and enabling rotation of said splint relative to said connector member lengthwise axis, wherein said splint outer end portion is movable radially away from or towards the patient's torso.

3. A shoulder orthosis as in claim 2, wherein said damper means consists of an assembly made of a piston rod axially engaging a hydraulic cylinder, said assembly integral to said extendible connector member, and of a means for continuously biasing said piston rod in extended condition away from said cylinder, said cylinder defining an outer end portion opposite said piston, and said piston rod defining a head opposition said cylinder.

4. A shoulder orthosis as in claim 3, wherein said damper means consists of a gas spring unit.

5. A shoulder orthosis as in claim 4, wherein said locking means consists of an elastic locking unit, cooperating with said gas spring unit, and a control member, controlling actuation of said locking means.

6. A shoulder orthosis as in claim 5, wherein said splint consists of:
  a) a channel member defining an arcuate panel, sized and shaped to conformingly receive and support a lower half portion of a patient's forearm, said arcuate panel having an inner end portion and an outer end portion, and a bed extending therebetween;
  b) forearm securing band members, integrally mounted to said arcuate panel intermediate said inner and outer end portions thereof and releasably engageable around an upper half portion of the patient's forearm; and
  c) a support anchor, integrally mounted transversely of said arcuate panel inner end portion and endwisely of said cylinder outer end portion.

7. A shoulder orthosis as in claim 6, wherein said rotating member consists of said piston rod being freely rotatably mounted axially within said cylinder, wherein during the patient's arm flexion and extension back and forth radially relative to the patient's torso and within the same horizontal plane, the pivotal axis of the patient's elbow remains coaxial at all times with the lengthwise axis of said piston rod and cylinder assembly.

8. A shoulder orthosis as in claim 6, wherein said belt member support section consists of an inner portion, shaped and sized to conformingly fit around the patient's trochanter portion, an integral outer pocket portion defining a pocket having a mouth, said piston rod head engaging through said pocket mouth and into said pocket, and a pivot mount member pivotally mounting said piston rod head to said pocket portion into said pocket and providing pivotal motion of said piston rod about an axis transverse to said piston and cylinder assembly lengthwise axis.

9. A shoulder orthosis as in claim 8, wherein said locking means control member is mounted remotely from said piston and cylinder assembly.

10. A shoulder orthosis as in claim 9, wherein said control member is mounted onto said belt member at a distance from said belt member support section.

11. A shoulder orthosis as in claim 8, wherein said forearm securing band members include adjustable hook and loop fastener means.

12. A shoulder orthosis as in claim 11, wherein said waist belt member includes adjustable hook and loop fastener means.

13. A shoulder orthosis as in claim 11, further including a palm rest tab, integrally projecting from said arcuate panel outer end portion, for supporting the patient's hand palm, and being slightly transversely inclined and making a large acute angle relative to said arcuate panel bed, wherein the patient's arm wrist is maintained in slight extension.

14. A shoulder orthosis as in claim 10, further including cushioning members, carried inwardly of said belt member and ergonomically conforming to the patient's waist hip.

15. A shoulder orthosis as in claim 11, wherein said palm rest tab further includes integral hand palm aeration bores.

16. A shoulder orthosis as in claim 15, wherein said arcuate panel inner end portion is of such a shape as to provide both a lateral support and an anteroposterior support for the patient's supported forearm.

17. A method of use of a shoulder orthosis for long term support of a patient's arm in postoperative shoulder immobilization abduction posture for injured rotator cuff muscle tear, said orthosis of the type comprising: a waist belt member, releasably attachable to the patient's waist line; an arm splint, defining opposite outer and inner end portions, and releasably attachable to the patient's arm; an extendible connector member, spacedly interconnecting a support section of said belt member to said splint inner end portion and defining a lengthwise axis thereof, wherein said splint is movable in translation between a frilly extended abduction first limit condition and a retracted adduction second limit condition, angularly relative to the patient's torso; a damper means for cooperating with said connector member in biasing said splint away from said belt member, wherein said damper means enables cyclical back and forth extension/retraction of said extendible connector member between said first and second limit conditions thereof; a locking means for releasably locking said extendible connector member at a selected condition thereof against the biasing force of said damper means; and a splint swing motion compensating means for providing transverse play of said connector member transversely of said lengthwise axis thereof, to accommodate inward rotation of the patient's arm naturally induced as the patient's arm is raised away from the patient's torso; said orthosis enabling cyclical exercising of the patient's arm healthy adductor muscles while minimising contraction of the injured muscles in the rotator cuff; wherein said method comprising the following steps:
  a) attaching said waist belt member to the patient's waist;
  b) securing the patient's arm to said arm splint;
  c) deactivating said locking means; and
  d) engaging the patient's adductor muscles to at least partly retract said connector member from said fully extended first limit condition towards said second limit condition.

18. A method of use of shoulder orthosis as in claim 17, further including the steps of:
  e) releasing the patient's adductor muscle engagement; and
  f) allowing said damper means to extend said connector member to return to said first fully extended limit condition.

19. A method of use as in claim 18, further including the step of: engaging once again the patient's adductor muscles to retract said connector member from said fully extended first limit condition towards its said second limit condition.

20. A method of use as in claim 19, further including the step of: rotating said arm support channel member relative to said waist belt member about said connector member, wherein flexion and extension of the patient's arm back and forth radially relative to the patient's torso on the same horizontal plane is achieved, and wherein the pivotal axis of the patient's elbow remains coaxial at all times with the lengthwise axis of said connector member.

* * * * *